United States Patent [19]

Hisamoto et al.

[11] Patent Number: 4,927,950
[45] Date of Patent: May 22, 1990

[54] FLUORINE-CONTAINING SILANE COMPOUNDS

[75] Inventors: Iwao Hisamoto, Suita; Masaru Hirai, Settsu; Sueyoshi Ishikawa, Kishiwada, all of Japan

[73] Assignee: Daikin Industries, Ltd., Osaka, Japan

[21] Appl. No.: 709,681

[22] Filed: Mar. 8, 1985

[30] Foreign Application Priority Data

Mar. 9, 1984 [JP] Japan .................. 59-46069

[51] Int. Cl.$^5$ .................. C07F 7/08; C07F 7/10; C07F 7/18
[52] U.S. Cl. .................. 556/419; 556/423; 556/427; 556/428; 556/440; 556/442; 556/445; 556/448; 549/215
[58] Field of Search ............... 556/427, 428, 419, 448, 556/445, 440, 442, 423; 549/215

[56] References Cited

U.S. PATENT DOCUMENTS

| | | | |
|---|---|---|---|
| 3,639,156 | 2/1972 | Pittman et al. .......... | 556/427 X |
| 3,716,517 | 2/1973 | Pittman et al. .......... | 556/427 X |
| 3,772,346 | 11/1973 | Hess .................. | 556/427 X |
| 3,794,672 | 2/1974 | Kim .................. | 556/427 |

*Primary Examiner*—Paul F. Shaver

[57] ABSTRACT

A fluorine-containing silane compound of the formula:

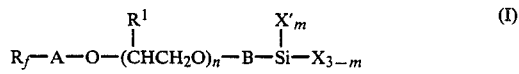

wherein $R_f$ is a fluorine-containing $C_4$—$C_{18}$ aliphatic group, $R^1$ is hydrogen or a $C_1$–$C_4$ alkyl group, A is a straight or branched $C_1$–$C_{12}$ alkylene group or a group of the formula:

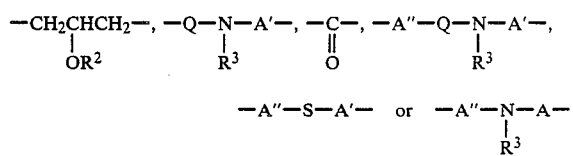

in which $R^2$ is hydrogen or a $C_1$–$C_3$ acyl group, $R^3$ is a $C_1$–$C_6$ acyl group, A' is a $C_2$–$C_8$ alkylene group, A" is a $C_1$–$C_4$ alkylene group, and Q is —CO— or —SO$_2$—, B is a group of the formula:

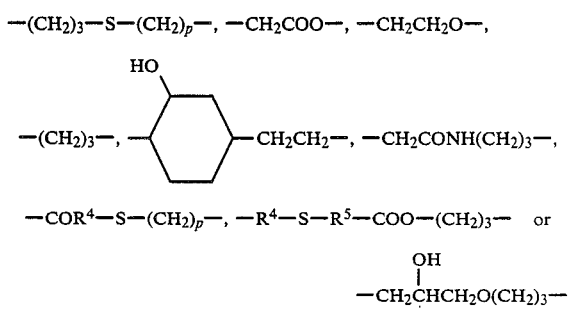

in which $R^4$ and $R^5$ are each a straight or branched $C_2$ or $C_3$ alkylene group, and p is 2 or 3, X is chlorine or a $C_1$–$C_3$ alkoxy group, X' is chlorine or a $C_1$–$C_3$ alkyl or alkoxy group, a phenyl group or a glycidyl group, m is 0 or 1, and n is an integer of 0 to 40, which modifies surface characteristics of a solid substrate.

4 Claims, No Drawings

FLUORINE-CONTAINING SILANE COMPOUNDS

FIELD OF THE INVENTION

The present invention relates to novel fluorine-containing silane compounds. More particularly, it relates to novel fluorine-containing silane compounds, a condensation product of the same with other silane coupling agent, a method for preparing the same and a solid surface modifier comprising the same.

BACKGROUND OF THE INVENTION

It is well known that application of a compound bearing fluorine-containing aliphatic groups on a solid substrate such as resins, resin compounds and fibers improves surface characteristics of the substrate, for example, non-tackiness, a leveling property, an anti-static property, a stain-proofing agent, a clouding or fog resistance, water- and oil-repellency, lubricity, etc.

The modification of the surface of the substrate is effected by applying the fluorine-containing compound on the surface or by compounding it in the substrate. However, application of the compound lacks durability while the compounding of the compound may deteriorate the inherent properties of the substrate.

SUMMARY OF THE INVENTION

One object of the present invention is to provide novel fluorine-containing silane compounds.

Another object of the invention is to provide a process for preparing the novel fluorine-containing silane compound.

Further object of the invention is to provide a condensation product of the novel fluorine-containing silane compound and other silane coupling agent.

Yet further object of the invention is to provide a solid surface modifier which can overcomes the disadvantages of the conventional fluorine-containing compound.

DETAILED DESCRIPTION OF THE INVENTION

According to one aspect of the present invention, there is provided a fluorine-containing silane compound of the formula:

$$R_f-A-O-(CHCH_2O)_n-B-Si-X_{3-m} \quad \text{(I)}$$
$$\overset{R^1}{|} \qquad\qquad\qquad \overset{X'_m}{|}$$

wherein
$R_f$ is a fluorine-containing $C_4$–$C_{18}$ aliphatic group,
$R^1$ is hydrogen or a $C_1$–$C_4$ alkyl group,
A is a straight or branched $C_1$–$C_{12}$ alkylene group or a group of the formula:

$$-CH_2CHCH_2-,\ -Q-N-A'-,\ -\overset{O}{\underset{\|}{C}}-,\ -A''-Q-N-A'-,$$
$$\overset{|}{OR^2}\qquad \overset{|}{R^3}\qquad\qquad\qquad \overset{|}{R^3}$$

$$-A''-S-A'-\ \text{or}\ -A''-N-A-$$
$$\qquad\qquad\qquad\qquad\overset{|}{R^3}$$

in which
$R^2$ is hydrogen or a $C_1$–$C_3$ acyl group, $R^3$ is a $C_1$–$C_6$ acyl group, A' is a $C_2$–$C_8$ alkylene group, A'' is a $C_1$–$C_4$ alkylene group, and Q is —CO— or —SO$_2$—, B is a group of the formula:

$$-(CH_2)_3-S-(CH_2)_p-,\ -CH_2COO-,\ -CH_2CH_2O-,$$

$$-(CH_2)_3-,\ -\underset{\text{(cyclohexyl with HO)}}{\diagram}-CH_2CH_2-,\ -CH_2CONH(CH_2)_3-,$$

$$-COR^4-S-(CH_2)_p-,\ -R^4-S-R^5-COO-(CH_2)_3-\ \text{or}$$

$$-CH_2CHCH_2O(CH_2)_3-$$
$$\overset{|}{OH}$$

in which
$R^4$ and $R^5$ are each a straight or branched $C_2$ or $C_3$ alkylene group, and p is 2 or 3,
X is chlorine or a $C_1$–$C_3$ alkoxy group,
X' is chlorine or a $C_1$–$C_3$ alkyl or alkoxy group, a phenyl group or a glycidyl group,
m is 0 or 1, and
n is an integer of 0 to 40.

In the specification, the fluorine-containing aliphatic group $R_f$ is intended to mean a straight or branched, unsubstituted or substituted aliphatic group which contains fluorine. The substituent may be hydrogen, chlorine and bromine. The backbone chain of the group may be interrupted by oxygen atom(s). Preferred fluorine-containing aliphatic group is one containing 4 to 18 carbon atoms and/or more fluorine atoms than carbon atoms.

Specific examples of the fluorine-containing silane compound (I) of the invention are as follows:

$$R_fCH_2CH(OH)CH_2O(CH_2CH_2O)_{10}CO(CH_2)_2S(CH_2)_3Si(OCH_3)_3 \quad (1)$$

$$R_fSO_2N(CH_2CH_2O)_{15}CH_2CONH(CH_2)_3Si(OC_2H_5)_3 \quad (2)$$
$$\overset{|}{C_3H_7}$$

$$R_f(CH_2)_2O(CH_2CH_2O)_{20}(CH_2)_3S(CH_2)_3Si(OCH_3)_2 \quad (3)$$
$$\overset{|}{CH_3}$$

$$R_f(CH_2)_2O(CH_2CH_2O)_5-\underset{\text{(cyclohexyl with HO)}}{\diagram}-(CH_2)_2SiOCH_3)_3 \quad (4)$$

$$R_f(CH_2)_2OCO(CH_2)_2S(CH_2)_3Si(OCH_3)_3 \quad (5)$$

$$R_f(CH_2)_2O(CH_2)_2S(CH_2)_2SiCl_3 \quad (6)$$

$$R_fCOO(CH_2CH_2O)_8COCHCH_2S(CH_2)_3Si(OC_2H_5)_3 \quad (7)$$
$$\overset{|}{CH_3}$$

$$R_f-CH_2CHCH_2O(CH_2CH_2O)_{10}COCHCH_2Si(CH_2)_3Si(OCOCH_3)_3 \quad (8)$$
$$\overset{|}{OCOCH_3}\qquad\qquad \overset{|}{CH_3}$$

$$R_f(CH_2)_2O(CH_2CH_2O)_5CH_2CHCH_2O(CH_2)_3Si(OCH_3)_3 \quad (9)$$
$$\overset{|}{OH}$$

The novel fluorine-containing silane compound (I) may be prepared by reacting a compound of the formula:

$$R_f-A-O-(CH_2CH_2O)_n-Y \quad (II)$$

wherein $R_f$, A and n are the same as defined above. Y is hydrogen or a group of the formula:

—CH$_2$COOH, —CH$_2$COOC$_2$H$_5$, —CH$_2$CH=CH$_2$, $$-CO-\underset{\underset{CH_3}{|}}{C}=CH_2, \quad -CO-CH=CH_2,$$

—CH$_2$CH$_2$OH or —CH$_2$CH$_2$SH with a silane compound of the formula:

$$\underset{Z-Si-X_{3-m}}{\overset{X'_m}{|}} \quad (III)$$

wherein X, X' and m are the same as defined above. Z is a group of the formula:

$$-(CH_2)_3SH, \; -CH=CH_2, \; -(CH_2)_3OCOC\underset{\underset{CH_3}{|}}{=}CH_2,$$

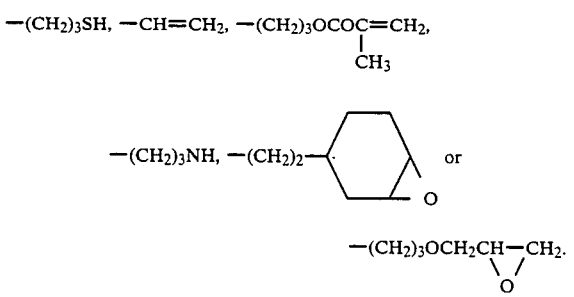

The reaction is carried out in the presence or absence of a solvent not containing water at a temperature of 50° to 150° C. for 4 to 12 hours preferably with stirring. The optionally used solvent are lower alcohols (e.g. methanol, ethanol, etc.), lower aliphatic ketones (e.g. acetone, etc.), lower aliphatic esters (e.g. ethyl acetate, etc.) and halogen-containing solvents (e.g. trichloroethane, etc.). Optionally, a catalyst such as alkaline quarternary ammonium salts (e.g. tetramethylammonium chloride, etc.), peroxides (e.g. t-butyl peroxypivalate, benzoil peroxide, etc.) and azo compounds (e.g. azobisisobutyronitrile, etc.) is used.

The fluorine-containing silane compound (I) modifies the surface characteristics and may be used as an fog resistant agent, a stain-proofing agent for hairs, a water- and oil-repellent for textiles or hairs, an SR agent, a dispersing agent for an inorganic filler (e.g. glass fiber, carbon, etc.), a leveling agent for resinous compounds, an anti-static agent, etc. Since the fluorine-containing silane compound (I) is nonionic, it does not deteriorate the inherent properties of the substrate when it is compounded in the solid substrate. Further, the compound (I) may have a softening effect on textiles.

The fluorine-containing silane compound (I) as such may be used as a modifier of the substrate surface. Furthermore, in view of shelf stability of the compound (I), it is dissolved or dispersed in the form of an organic solvent in a concentration of 0.1 to 5% by weight. Specific examples of the organic solvent are trichloroethane, trichlorotrifluoroethane, ethyl acetate, toluene, etc. The compound (I) may be used as an aqueous solution or dispersiion. In this instance, the compound (I) containing not less than 8 alkyleneoxy units are preferred since it has self-solubility of -dispersibility in water. The compound (I) containing less than 8 alkyleneoxy units may be dispersed in water by the aid of an emulsifier. Specific examples of the emulsifier are polyoxyethylene alkylphenyl ethers, polyoxyethylene sorbitol aliphatic acid esters, polyoxyethylene sorbitan aliphatic acid esters, etc.

Among the surface characteristics of the substrate, the anti-static property, fog resistance and SR property are preferably improved by the fluorine-containing compound (I) containing not less than 8 alkyleneoxy units. However, a condensation product of the fluorine-containing compound (I) containing less than 8 alkyleneoxy units with a hydrophilic organic silane coupling agent has the same modifying ability as that containing not less than 8 alkyleneoxy units.

Water- and oil-repellency is preferably improved by the fluorine-containing silane compound (I) containing 0 to 5 alkyleneoxy units and bearing $R_f$ with not less than 8 carbon atoms.

In order to improve the durability of the modified surface characteristics, the fluorine-containing silane compound (I) is compounded in the substrate or applied silane coupling agent or in the form of the condensation product. The condensation may be carried out before application or on the surface by firstly applying the silane coupling agent and then the compound (I) to undergo condensation on the surface. When the compound (I) is condensated with the silane coupling agent, the former may be hydrolyzed to a silanol compound. In addition, the fluorine-containing silanol compound (I) as such can form a condensation product. The condensation may be carried out by a per se conventional method (cf. A. G. Pittman, W. L. Wasley and J. N. Roitman, Text. Chem. Colorist, 4, 278 (1972).

The kinds of the substituents born by the fluorine-containing compound (I) may be selected according to the end use and/or the kind of the substrate. The compound (I) may be used in the form of a mixture or the condensation product with other organic silane compounds so as to increase the modifying property and durability of the compound (I).

Specific examples of the organic silane compound to be used together or condensated with the compound (I) are CH$_2$=CHSiCl$_3$, CH$_2$=CHSi(OC$_2$H$_4$OCH$_3$)$_3$, CH$_2$=CHSi(OC$_2$H$_5$)$_3$, CH$_2$=CHSi(OCH$_3$)$_3$, $$CH_2=\underset{\underset{CH_3}{|}}{C}-COO-(CH_2)_3Si(OCH_3)_3,$$

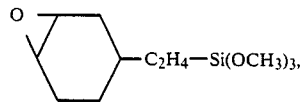

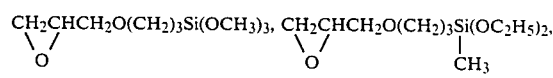

H$_2$NC$_2$H$_4$NH(CH$_2$)$_3$Si(OCH$_3$)$_3$, H$_2$NC$_2$H$_4$NH(CH$_2$)$_3$Si(OCH$_3$)$_2$,
$\qquad\qquad\qquad\qquad\qquad\qquad\qquad\qquad\qquad\quad |$
$\qquad\qquad\qquad\qquad\qquad\qquad\qquad\qquad\qquad\; CH_3$

HS(CH$_2$)$_3$Si(OCH$_3$)$_3$,

-continued

CH$_3$O(CH$_2$CH$_2$O)$_z$-(CH$_2$)$_3$SiCl$_3$ (z = 1–40), Cl(CH$_2$)$_3$Si(OCH$_3$)$_3$,

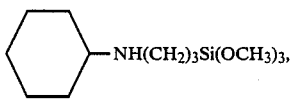

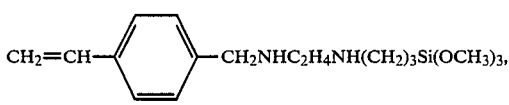

CH$_3$Si(OCH$_3$)$_3$, n-C$_{18}$H$_{37}$Si(OCH$_3$)$_3$,

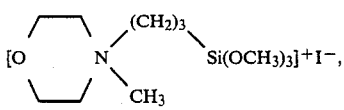

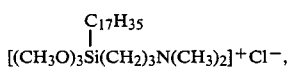

[(CH$_3$O)$_3$Si(CH$_2$)$_3$N(CH$_3$)$_2$]$^+$Cl$^-$,

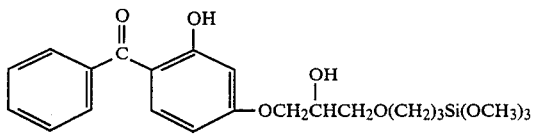

The fluorine-containing organic silane compound (I) of the invention, alone or as a mixture, is compounded in the substrate as the antistatic agent, the fog resistant, the SR agent and the like in an amount of 0.005 to 2% by weight based on the weight of the substrate.

The present invention will be hereinafter explained further in detail by following Examples in which parts and % are by weight.

EXAMPLE 1

In a 200 ml four-necked flash equipped with a thermometer, a condenser and a stirrer,

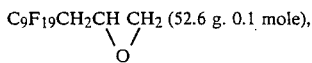

$$HO(CH_2CH_2O)_{10}CO\underset{\underset{CH_3}{|}}{C}=CH_2 \quad (52.6 \text{ g, 0.1 mole})$$

and, as a catalyst, BF$_3$-ether complex (0.26 g) were charged and stirred on a water bath kept at 70° C. for 8 hours. Gas chromatographic analysis confirmed disappearance of the raw epoxy compound (column: Silicone SE-30, 1 m. Column temperature being raised from 100° to 250° C.). Peak at 1,640 cm$^{-1}$ in IR spectrum showed presence of double bonds. After filtering materials insoluble in methanol, the reaction mixture was washed with n-hexane and dried under reduced pressure to obtain a transparent liquid intermediate,

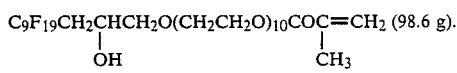

Yield 92%.

| Elemental analysis: | C | H | O | F |
|---|---|---|---|---|
| Calc'd: | 41.1% | 4.8% | 19.8% | 34.3% |
| Found: | 40.8% | 4.9% | 20.6% | 33.7% |

In a 500 flask, the thus obtained intermediate (52.6 g, 0.05 mole), HS(CH$_2$)$_3$Si(OCH$_3$)$_3$ (9.8 g, 0.05 mole) and absolute ethyl acetate (250 g) were charged. After replacing the interior of the flask with nitrogen, the mixture was heated on a water bath kept at 70° to 75° C. with stirring. Then, as a radical initiator, perbutyl pivalate (0.6 g) was added to initiate the reaction and the mixture was reacted at the same temperature with stirring. According to gas chromatographic analysis, absence of free methanol and disappearance of the thiol compound were confirmed. In IR spectrum, disappearance of peak at 1,720 cm$^{-1}$ corresponding to the double bonds was found. After removing ethyl acetate, the reaction mixture was washed with n-hexane and dried under reduced pressure to obtain a transparent viscous liquid compound,

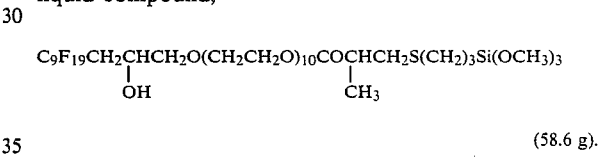

(58.6 g).

M.P. 8°–12° C. B.P. 200° C. Yield 94%.

EXAMPLE 2

In a 200 ml flask, a fluorine-containing nonionic surfactant,

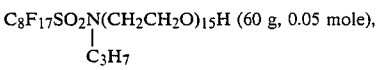

ClCH$_2$COOC$_2$H$_5$ (6.1 g, 0.05 mole), dimethylformamide (100 ml) and triethylamine (5.1 g) were charged and stirred at 90° C. for 5 hours. The resultant solution was filtered to remove triethylamine hydrochloride, and the filtrate was dried under reduced pressure, washed with n-hexane and again dried to obtain a transparent viscous liquid intermediate,

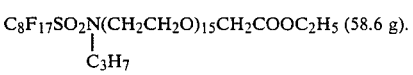

Yield 91%.

In the 200 ml flask, the thus produced intermediate (51.5 g, 0.04 mole), H$_2$N(CH$_2$)$_3$Si(OC$_2$H$_5$)$_3$ (8.9 g, 0.04 mole) and absolute ethanol (20 ml) were charged and stirred on a water bath kept at 90° C. for 5 hours. The reaction mixture was dired under reduced pressure, washed with a ethanol/n-mixture and again dried under reduced pressure to obtain a transparent viscous liquid compound,

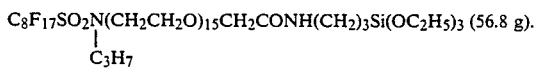$C_8F_{17}SO_2N(CH_2CH_2O)_{15}CH_2CONH(CH_2)_3Si(OC_2H_5)_3$ (56.8 g).
  |
  $C_3H_7$ M.P. 11°–15° C. B.P. 200° C. Yield 94%.

EXAMPLE 3

In the 200 ml flask, dry $C_{11}F_{23}CH_2CH_2O(CH_2CH_2O)_5H$ (83.4 g, 0.1 mole),

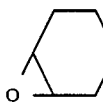—$CH_2CH_2Si(OCH_3)_3$ (52.8 g, 0.2 mole)

and tetramethyl ammonium chloride (0.4 g) were charged and stirred in a nitrogen atmosphere at 80° C. for 10 hours. The reaction mixture was dissolved in trichlorotrifluoroethane and filtered to remove insoluble materials. The filtrate was dried under reduced pressure, washed with n-hexane and again dried under pressure to obtain

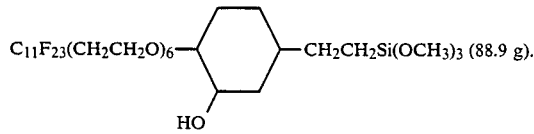
$C_{11}F_{23}(CH_2CH_2O)_6$—⌬—$CH_2CH_2Si(OCH_3)_3$ (88.9 g).
               |
              HO M.P. 5°–7° C. Yield 81%.

EXAMPLE 4

In a one liter flask, a fluorine-containing surfactant, $C_{10}F_{21}CH_2CH_2O(CH_2CH_2O)_{20}H$ (144.4 g, 0.1 mole) and absolute tetrahydrofuran (400 ml) were charged and, in a nitrogen atmosphere, NaH (4.6 g, 0.12 mole) was gradually added. After addition of NaH, the mixture was stirred at 60° C. for 2 hours, and then allyl bromide (18.2 g, 0.15 mole) was added and heated for 15 hours with stirring. Excess NaH and formed NaBr were filtered, and tetrahydrofuran and excess allyl bromide were distilled off to obtain an intermediate, allyl ether (114.8 g).
Yield 97%.

In a 500 ml flask, the thus produced allyl ether

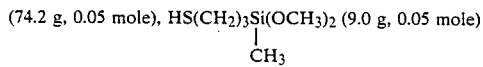
(74.2 g, 0.05 mole), $HS(CH_2)_3Si(OCH_3)_2$ (9.0 g, 0.05 mole)
                                        |
                                       $CH_3$ and absolute ethyl acetate (333 g) were charged and heated on a water bath kept at 70° C. in a nitrogen atmosphere. To the mixture, perbutyl pivalate (1.0 g) was added and reacted for 8 hours with stirring. The completion of the reaction was confirmed in the same manner as in Example 1. The reaction mixture was purified in the same manner as in Example 1 to obtain a transparent viscous liquid compound,

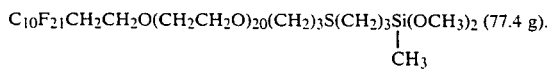
$C_{10}F_{21}CH_2CH_2O(CH_2CH_2O)_{20}(CH_2)_3S(CH_2)_3Si(OCH_3)_2$ (77.4 g).
                                                  |
                                                 $CH_3$ M.P. 17°–21° C. Yield 93%.

EXAMPLE 5

In the 500 ml flask, $C_9F_{19}CH_2CH_2OCOCH=CH_2$ (56.8 g, 0.1 mole), $HS(CH_2)_3Si(OCH_3)_3$ (19.6 g, 0.1 mole) and ethyl acetate (306 g) were charged and heated to 70° C. in a nitrogen atmosphere. Then, perbutyl pivalate (1.1 g) was added and stirred at the same temperature for 6 hours. After distilling ethyl acetate off under reduced pressure and washing with n-hexane, the reaction mixture was dried under reduced pressure to obtain $C_9F_{19}CH_2CH_2OCOCH_2CH_2S(CH_2)_3Si(OCH_3)_3$ (72.6 g).
M.P. 27°–28° C. Yield 95%.

EXAMPLE 6

2% aqueous solution of following Compound (a) of Mixture (b) was prepared:

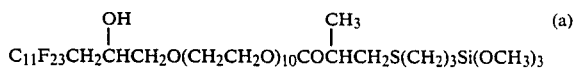
$$\underset{|}{OH} \qquad \underset{|}{CH_3} \qquad (a)$$
$C_{11}F_{23}CH_2CHCH_2O(CH_2CH_2O)_{10}COCHCH_2S(CH_2)_3Si(OCH_3)_3$

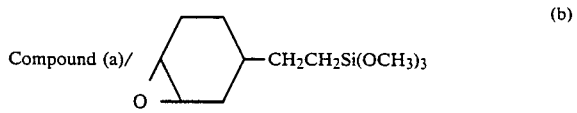
Compound (a)/ ⌬—$CH_2CH_2Si(OCH_3)_3$ (b)
              |
              O (weight ratio, 80/20) (100 parts) and $Zn(BF_4)_2$ (0.5 part).

In the solution, #40 cotton broadcloth was dipped, and the solution was squeezed out. The cloth was dried at 110° C. for 3 minutes and examined for water-repellency, oil-repellency and washability. Water-repellency was examined by a spray method according to JIS (Japanese Industrial Standards) 1005, oil-repellency was examined according to AATCC-TM 118-1966 and washability was evaluated by reflectance measured according to JIS L0217-1976, Annexed Table 1, Washing method No. 103.

The results are shown in Table 1.

TABLE 1

|  | Untreated | Compound (a) | Mixture (b) |
|---|---|---|---|
| Initial |  |  |  |
| Water-repellency | 0 | 0 | 0 |
| Oil-repellency | 0 | 4 | 5 |
| Washability | 40 | 76 | 71 |
| After 20 times washing |  |  |  |
| Water-repellency | 0 | 0 | 0 |
| Oil-repellency | 0 | 1 | 3 |
| Washability | 42 | 78 | 74 |

EXAMPLE 7

By using following Mixture (c) and Solution (d), the same tests were repeated with Nylon knit jersey cloth:
(c) A mixture of a 2% solution of

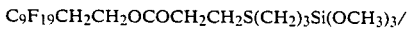
$C_9F_{19}CH_2CH_2OCOCH_2CH_2S(CH_2)_3Si(OCH_3)_3$/

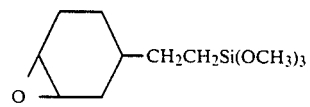
⌬—$CH_2CH_2Si(OCH_3)_3$
|
O in a weight ratio of 80/20 in a mixture of tetrahydrofuran and water in a volume ratio of 90/10 (100 parts) and $Zn(BF_4)_2$ (0.5 part)

(d) a 2% solution of

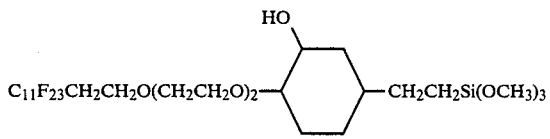

in a mixture of tetrahydrofuran and water in a volume ratio of 90/10.

In this Example, 500 time rubbing was carried out according to JIS L0849-1967.

The results are shown in Table 2.

TABLE 2

|  | Compound (a) | Mixture (b) |
|---|---|---|
| Initial |  |  |
| Water-repellency | 100 | 80 |
| Oil-repellency | 6 | 5 |
| After 20 time washing |  |  |
| Water-repellency | 80 | 50 |
| Oil-repellency | 3 | 1 |
| After 500 time rubbing |  |  |
| Water-repellency | 80 | 50 |
| Oil-repellency | 7 | 1 |

EXAMPLE 7

In silicone rubber (100 parts), a cross-linking agent, Perhexa 2,5B (0.5 part, manufactured by Nippon Fat and Oil) and following Compound (e), (f) or (g) were compounded and kneaded with rolls to form a sheet (10 cm × 10 cm × 3 mm).

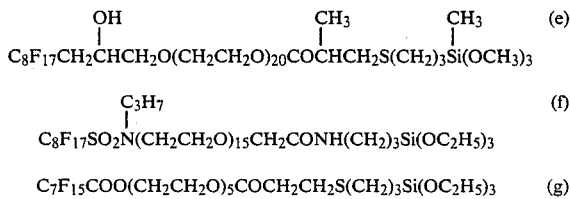

With hanging the sheet in midair by holding its periphery, a pair of electrodes were positioned on both sides of the sheet at a distance of about 1 cm. Then, a potential of −9,000 V was applied between the electrodes for one minute. After 30 seconds, the potential on the sheet surface was measured. The results are shown in Table 3.

TABLE 3

| Compound | Surface potential (V) |
|---|---|
| (e) | −480 |
| (f) | −510 |
| (g) | −670 |
| None | −860 |

What is claimed is:

1. A fluorine-containing silane compound of the formula:

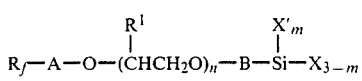

wherein $R_f$ is a fluorine-containing $C_4$–$C_{18}$ aliphatic group,
$R^1$ is hydrogen or a $C_1$–$C_4$ alkyl group,
A is a straight or branched $C_1$–$C_{12}$ alkylene group or a group of the formula:

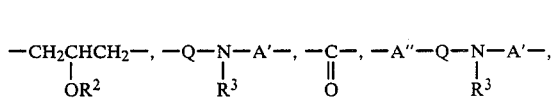

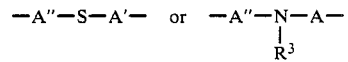

in which
$R^2$ is hydrogen or a $C_1$–$C_3$ acyl group, $R^3$ is a $C_1$–$C_6$ acyl group, A' is a $C_2$–$C_8$ alkylene group, A" is a $C_1$–$C_4$ alkylene group, and Q is —CO— or —SO$_2$—,
B is a group of the formula:

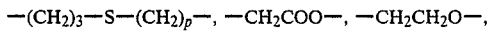

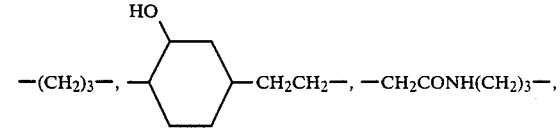

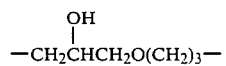

in which
$R^4$ and $R^5$ are each a straight or branched $C_2$ or $C_3$ alkylene group, and p is 2 or 3,
X is chlorine or a $C_1$–$C_3$ alkoxy group,
X' is chlorine or a $C_1$–$C_3$ alkyl or alkoxy group, a phenyl group or a glycidyl group,
m is 0 or 1, and
n is an integer of 5 to 40.

2. The silane compound according to claim 1, wherein the fluorine-containing aliphatic group is one containing 4 to 18 carbon atoms and/or more fluorine atoms than carbon atoms.

3. A process for preparing a fluorine-containing silane compound of the formula:

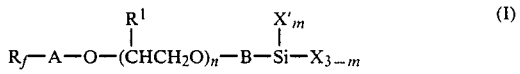

wherein
$R_f$ is a fluorine-containing $C_4$–$C_{18}$ aliphatic group,
$R^1$ is hydrogen or a $C_1$–$C_4$ alkyl group,
A is a straight or branched $C_1$–$C_{12}$ alkylene group or a group of the formula:

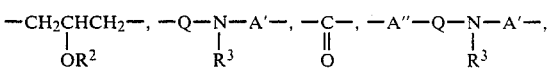

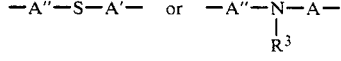

in which
$R^2$ is hydrogen or a $C_1$–$C_3$ acyl group, $R^3$ is a $C_1$–$C_6$ acyl group, A' is a $C_2$–$C_8$ alkylene group, A" is a $C_1$–$C_4$ alkylene group, and Q is —CO— or —SO$_2$—,
B is a group of the formula:

—(CH₂)₃—S—(CH₂)ₚ—, —CH₂COO—, —CH₂CH₂O—,

—(CH₂)₃—⟨cyclohexyl-OH⟩—CH₂CH₂—, —CH₂CONH(CH₂)₃—,

—COR⁴—S—(CH₂)ₚ—, —R⁴—S—R⁵—COO—(CH₂)₃— or

—CH₂CH(OH)CH₂O(CH₂)₃— in which
R⁴ and R⁵ are each a straight or branched C₂ or C₃ alkylene group, and p is 2 or 3,
X is chlorine or a C₁-C₃ alkoxy group,
X' is chlorine or a C₁-C₃ alkyl or alkoxy group, a phenyl group or a glycidyl group,
m is 0 or 1, and
n is an integer of 5 to 40
by reacting a compound of the formula $$R_f\text{—A—O—}(CH_2CH_2O)_n\text{—Y} \quad (II)$$

wherein
$R_f$, A and n are the same as defined above, Y is hydrogen or a group of the formula:

—CH₂COOH, —CH₂COOC₂H₅, —CH₂CH=CH₂,

—CO—C(CH₃)=CH₂, —CO—CH=CH₂,

—CH₂CH₂OH or —CH₂CH₂SH with a silane compound of the formula:

$$\begin{array}{c} X'_m \\ | \\ Z\text{—Si—}X_{3-m} \end{array} \quad (III)$$

wherein
X, X' and m are the same as defined above and Z is a group of the formula:

—(CH₂)₃SH, —CH=CH₂, —(CH₂)₃OCOC=CH₂, —(CH₂)₃NH

-continued

—(CH₂)₂—⟨epoxycyclohexyl⟩ or —(CH₂)₃OCH₂CH—CH₂ with CH₃
                                                    \O/ wherein when
Y is —CH₂COOH, then Z is

—(CH₃)SH,
—(CH₂)₃NH₂,

—(CH₂)₂—⟨epoxycyclohexyl⟩, or

—(CH₂)₃OCH—CH₂,
         \O/

Y is —CH₂COOC₂H₅, then Z is —(CH₂)₃NH₂,
Y is
  —CH₂CH=CH₂, or
  —COC(CH₃)=CH₂, or
  —COCH=CH₂,
then Z is
  —(CH₃)SH, or
  —CH=CH₂, or
  —(CH₂)₃OCOC(CH₃)=CH₂,
Y is —CH₂CH₂OH, then Z is —(CH₂)₂—⟨epoxycyclohexyl⟩, or

—(CH₂)₃OCH—CH₂,
         \O/

Y is —CH₂CH₂SH, then Z is

CH=CH₂,
—(CH₂)₃OCOC(CH₃)=CH₂,

—(CH₂)₂—⟨epoxycyclohexyl⟩, or

4. A process according to claim 3, wherein the reaction temperature is from 50° to 150° C.

* * * * *